United States Patent [19]

Beall et al.

[11] 3,932,141

[45] Jan. 13, 1976

[54] APPARATUS FOR DETERMINING IMMUNOASSAYS OF ANTIGENS AND THEIR ANTIBODIES

[75] Inventors: Glenn Lee Beall, Gurnee; John Dennis Dodge, Arlington Heights; Robert Francis Koschalk, Zion; Emil Henry Soika, Lindenhurst, all of Ill.

[73] Assignee: Abbott Laboratories, North Chicago, Ill.

[22] Filed: July 10, 1974

[21] Appl. No.: 487,350

[52] U.S. Cl. ............... 23/259; 23/230 B; 23/253 R; 141/325; 221/289; 221/307; 424/1; 424/12; 428/403
[51] Int. Cl.² ......................................... G01N 33/16
[58] Field of Search ............. 23/230 B, 253 R, 259; 424/12; 221/289, 307; 141/234, 237, 325

[56] References Cited
UNITED STATES PATENTS

| | | | |
|---|---|---|---|
| 3,166,216 | 1/1965 | Guarr | 221/289 |
| 3,243,081 | 3/1966 | Schmank | 221/289 X |
| 3,389,966 | 6/1968 | Saravis | 424/12 X |
| 3,390,962 | 7/1968 | Goldsmith | 424/12 X |
| 3,409,172 | 11/1968 | Fuglsang-Madsen | 221/289 X |
| 3,692,491 | 9/1972 | Trentelman | 23/230 B |
| 3,725,004 | 4/1973 | Johnson | 23/230 B |
| 3,840,149 | 10/1974 | Zeller | 221/289 X |
| 3,843,450 | 10/1974 | Saxholm | 23/230 B |

Primary Examiner—Morris O. Wolk
Assistant Examiner—Sidney Marantz
Attorney, Agent, or Firm—Robert L. Niblack; Vincent A. Mallare

[57] ABSTRACT

A test apparatus for the determination of immunoassays of antigens and their antibodies which comprises a receptacle tray having a plurality of wells for receiving and samples, a holder for receiving and holding balls, coated with an immunologic composition and for depositing the balls into the wells of said receptacle tray, a ball-release piece fitting over one end of the holder, the ball-release piece being arranged to release the balls from the holder when pressed, and a cap to fit on the open end of the ball-release piece.

10 Claims, 7 Drawing Figures

U.S. Patent  Jan. 13, 1976  3,932,141
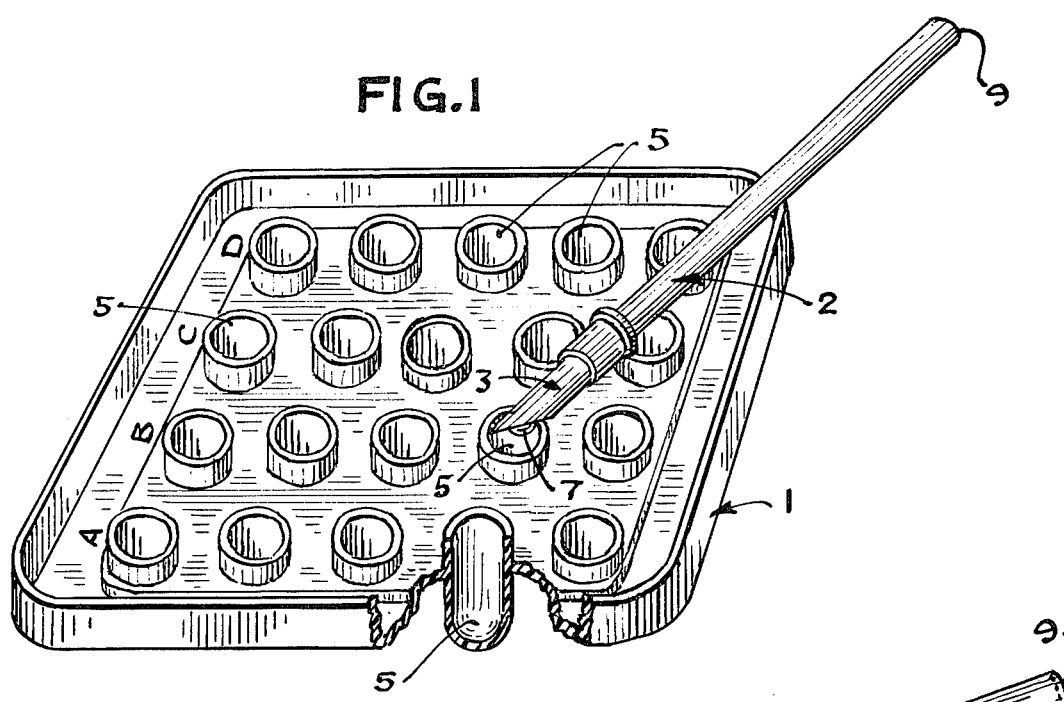
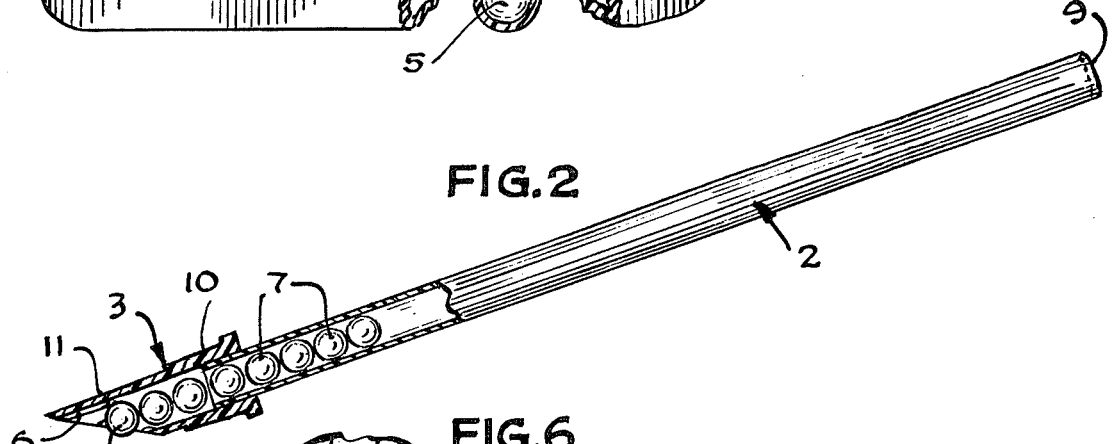
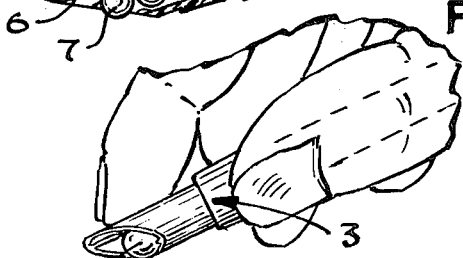
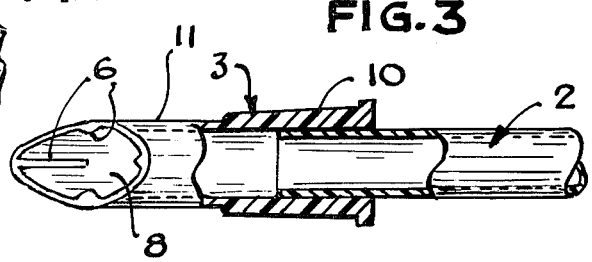
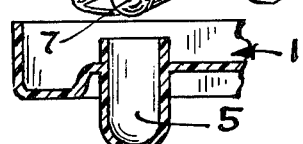
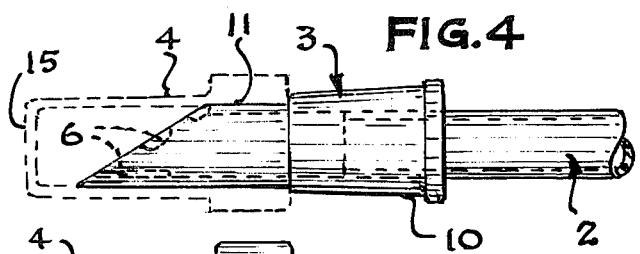
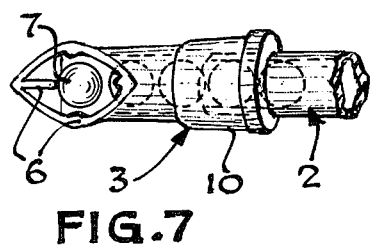
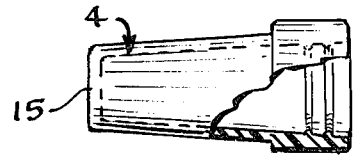

APPARATUS FOR DETERMINING IMMUNOASSAYS OF ANTIGENS AND THEIR ANTIBODIES

BACKGROUND OF THE INVENTION

This invention relates to diagnostic apparatus for use in radioimmunoassay for antigens and their antibodies. More particularly, this invention relates to a diagnostic apparatus for a direct radioimmunoassay for determining hapatitis associated antigen or its antibodies or antigens and antibodies.

Although there have been methods for determining the presence of antigenically active macromolecules such as intact viruses, virus capsids, subunits, bacteria, membranes, cell walls, hormones, etc., there has been a lack of a simple yet sensitive test method and apparatus for determining the presence of these materials. Viral hepatitis, including so called serum hepatitis, which is a relatively common disease, has not been heretofore easily detected by a sensitive test which is both specific and reproducible for quickly determining whether or not the serum from a patient or a donor contains hepatitis associated antigens or antibodies.

Furthermore, radioimmunoassay techniques have been developed in the past for various antigen-antibody materials. However, these radioimmunoassay techniques, such as disclosed in articles by Kevin Catt et al. in the *Journal of Biochemistry*, 1966, Volume 100, pages 31c and 33c and in *Science*, Volume 158, page 1570, 1967, are an indirect radioimmunoassay technique wherein the amount of antigen present is roughly proportional to the amount of radiation emitted by the tracer material. These procedures required the use of correlation tables and other materials which generally rendered the results less than reproducible and exact.

According to the present invention, it has been discovered that the above-noted difficulties, i.e., lack of reproducibility and exactness, have been overcome by utilizing the present diagnostic apparatus with the associated radioimmunoassay technique.

More specifically, the diagnostic test apparatus of the present invention comprises a receptacle tray having a series of wells for receiving samples, a holder arranged to receive, hold and deposit coated balls into the wells of the tray, a ball-release piece fitting over one end of the holder which is arranged when pressed to release the balls from the holder, and a cap to fit over the open end of the ball-release piece.

Other objects and advantages of the diagnostic test apparatus of the present invention will become more apparent from the following detailed description when taken in conjunction with the figures wherein:

FIG. 1 is a perspective view of the test apparatus of the present invention;

FIG. 2 is a partial-sectional side view of the holder and ball-release piece fitted on one end of the holder, illustrating the coated balls being held in the holder; and ball-release piece;

FIG. 3 is an enlarged partial-sectional, plan view of the ball-release piece on the end of the holder;

FIG. 4 is a partial cut-away side view of the assembled holder, ball-release piece and cap;

FIG. 5 is a partial-sectional view of the cap;

FIG. 6 is an enlarged side view of the ball-release piece on the end of the holder, illustrating the release of a coated ball from the ball-release piece; and FIG. 7 is a plan view of the ball-release piece on the holder, illustrating the configuration of the ball-release piece when pressed to release a coated ball.

Referring to FIGS. 1 and 4, the test apparatus of the present invention comprises a receptacle tray 1, a ball holder 2, a ball-release piece 3 and a cap 4 that fits over the ball-release piece. The receptacle tray 1 has a plurality of wells 5, which are arranged to receive samples of blood or serum, and balls 7 which are coated with an immunologic composition and which are to be used in determining the presence of hepatitis antigens in the samples of blood or serum. The wells 5 are of sufficient depth and size to hold a coated ball 7 and a sample of blood. The receptacle tray 1 may have a series of wells 5 from as few as six to nine wells to as many as 50 to 60 wells, depending on the size of the receptacle tray desired. The wells 5, as shown, may be arranged in rows which are parallel to one another and arranged so that the tray 1 can be placed on a flat surface when the coated balls and samples are deposited in the respective wells 5.

The ball holder 2 is a hollow tube with one end 9 closed, of a diameter larger than that of the coated balls or beads 7 so they can move through the tube with little resistance. The coated balls 7 are loaded by a conventional method into the tube 2 through the end opposite the closed end 9. As many balls 7 that are able to be fitted into tube 2 are loaded therein. The beads 7 are loaded by a means where they are not contaminated.

The ball-release piece 3 includes a flange portion 10 arranged to fit over one end of the ball holder tube 2. Extending from the flanged end of the ball-release 3 is a reduced portion 11 which has a beveled opening 8 through which the coated balls 7 are released into the wells 5. As shown, particularly in FIGS. 3 and 7, on the inner circumferential edge of the opening 8 there are a series of nibs 6 which restrict the movement of the coated balls 7 through the opening 8. The balls 7 are released from the ball-release piece 3 through the opening 8 when the piece 3 is pressed at the beveled opening 8 near the lower nib 6 as illustrated in FIG. 6. Accordingly, when it is desired to deposit one of the coated balls 7 into one of the wells 5 of the receptacle tray 1, the beveled end 11 of the ball-release 3 at the opening 8 is pressed on its extended exterior surface to release a ball into a well 5.

As shown in FIG. 4, a cap 4 is provided to fit snugly over the reduced beveled end 11 of the ball-release piece 3. The cap 4 has a flange portion 13 which is arranged to fit over the flange portion 10 of the ball-release 3. The cap 4 has a closed end 15 to prevent the release of any of the coated balls 7 when not needed or when the apparatus is not in use.

The receptacle tray 1 is preferably made of a plastic material which is durable and can be easily molded into the configuration shown in the drawings. The holding tube 2 and ball-release 3 as well as the cap 4 are preferably made of a durable plastic material which may be transparent to the eye. However, it is not necessary that the pieces be transparent except for the holding tube 2. The balls or beads 7 should be made of a material, i.e., plastic, which will not float in the sample of blood or serum in which it is placed in the wells 5. A plastic material which has been sound to be satisfactory for the balls 7 is polystyrene.

The wells 5 are of such a contour as to provide coverage of the balls 7 with a minumum sample of blood or serum while large enough so as to prevent the entrapment of air between the ball and well. With this arrangement, the sample is able to come into contact with the ball surface and to flow adequately between the ball and well.

The size of the receptacle tray 1 may be any size desired, such as a tray having as few as six to nine wells or as many as 50 to 60 wells. The holding tube 2 may be any length, but is preferably of a sufficient length to hold several balls or an amount of balls equal to the number of wells 5 in the receptacle tray 1. The ball-release piece 3 and cap 4 are made of a corresponding size to fit snugly over the holding tube 2 and ball-release piece 3, respectively.

In order to form the apparatus of the present invention, the polystyrene balls 7 must be coated with either an antigen or antibody. A hepatitis associated antibody solution of anti-australia antigen having a concentration of about 1 to about 100 micrograms of protein per milliliter is prepared in from about 0.005 to about 0.02 molar Tris-HCl, i.e., 2-amino-2-hydroxymethyl-1,3-propanediol-HCl utilizing an anti-australia antigen serum. The Tris-HCl buffers the solution to a pH from about 7.1 to about 9.5 along with about 0.01 percent to about 0.05 percent sodium azide. One milliliter of this hepatitis associated antibody is then coated on the balls surfaces by incubating at room temperature from about 6 to 72 hours. These coated polystyrene balls 7 are then washed with about 0.05 to about 0.02 molar Tris-HCl at a pH of 6.9 to 8.4 plus from about 0.01 percent to about 0.05 percent sodium azide. Following this washing and rinsing step, test bodies may be stored at 4°C. until necessary for use for radioimmunoassay.

It is preferred to utilize a 0.01 molar solution of Tris-HCl hydrochloride and 0.2 percent sodium azide buffered at a pH of 7.1 for both the incubation medium and the washing medium.

The amount of antibody coated on the surfaces of the polystyrene balls is preferably one thin layer. No standard curves or charts are necessary for the tests of the present invention; therefore, no specific amount of antigen in the coating is required as long as two similar balls are used.

Although the diagnostic apparatus of the present invention can be used for determining the presence of any appropriate antigen or its antibody by a simple yes-no technique, the use of the apparatus of the present invention will now be described with respect to the procedure for determining the presence of hepatitis associated antigen.

According to the present invention, the cap 4 is removed from the holding tube 2 that contains the antibody coated balls 7 and the ball-release piece 3 is held over the top of the receptacle tray 1 directly over a well 5 and a ball 7 is released therefrom by pressing down on the extended exterior of the release-piece 3 with the index finger, into a well 5 for each sample to be tested. Then, by using precision pipettes, there is added 0.2 milliliters of serum or blood and positive and negative controls on the bottom of the respective wells 5. It is important to make certain that each antibody coated ball 7 is completely surrounded by the serum or blood sample. To insure this, the tray 1 should be lightly tapped to release any air bubbles that may be trapped in the serum sample. After the balls 7, with the serum samples, have been placed in the respective wells 5 of the tray 1, a cover seal is applied to the tray 1 which is then incubated in a 45°C. water bath for two hours. At the end of the two hours, the tray is removed from the water bath and the cover sealer is removed and discarded.

With the use of a semi-automated aspiration and rinsing system and an automatic delivery system and vacuum source, each well 5 and ball 7 is rinsed with a total of 5 milliliters of distilled or deionized water. This wash procedure should be repeated one additional time. After this washing procedure, 0.2 milliliters of $^{125}I$-hepatitis associated antibodies (Human) are deposited in the bottom of each well 5. It is important that the antibody coated balls 7 are completely surrounded by the labeled antibody solution. As done before, the tray 1 is tapped to release any air bubbles that may be trapped in the solution. Then, a new cover sealer is placed on the tray and the tray is incubated in a 45°C. water bath for one hour. At the end of this period, the tray is removed from the water bath and the cover sealer is removed and discarded. Then, the antibody solution from each well 5 is aspirated and each well 5 and antibody coated bead 7 therein is rinsed with a total of 5 milliliters of distilled or deionized water as done before.

After being rinsed, the beads 7 are transferred from their respective wells to a properly identified counting tube which is arranged in a rack of oriented counting tubes. The beads 7 are transferred to the tubes by first invertedly aligning the rack of tubes over the receptacle tray 1 and then pressing the tubes tightly over the wells. With the tray inverted together with the tubes, the beads 7 fall into the properly labeled tubes. The counting tubes are then placed in a suitable well type gamma scintillation counter to determine the count rate. The position of the bead at the bottom of the counting tube is not important. Although it is not critical that the counting be done immediately, it should be performed as soon as possible. All control samples and unknowns must be counted together. The amount of radiation is recorded and compared with a control sample which has been run simultaneously, in order to determine the background count rate. The unknown test samples for the count rate, above that of the background rate, would be considered antigen positive providing a simple yes-no test without resorting to correlation tables and graphs.

While the test apparatus of the present invention has been utilized by way of the foregoing embodiment, the test apparatus of the present invention should be in no way limited thereto, but should be construed as broadly as any and all equivalents of the appended claims.

What is claimed is:

1. A test apparatus for use in a direct radioimmunoassay for antigens or antibodies comprising:
   a receptacle tray having a plurality of wells for receiving samples;
   balls coated with an immunologic composition;
   a ball holder having a first end and a second end, said holder arranged to receive and hold said coated balls and to deposit the balls into said wells of said receptacle tray; and
   a ball-release piece arranged to fit over the first end of said ball holder, said ball-release piece having an opening arranged to release said balls therefrom when said ball-release piece is pressed on its extended exterior surface.

2. A test apparatus according to claim 1, wherein a cap is provided to fit over the opening of said ball-release piece.

3. A test apparatus according to claim 1, wherein said receptacle tray has a series of wells arranged in rows parallel to each other.

4. A test apparatus according to claim 1, wherein said ball holder is a hollow tube with a closed second end.

5. A test apparatus according to claim 1, wherein said ball-release piece has a beveled open end with a series of nibs spaced along the inner circumferential edge of said beveled opening.

6. A test apparatus according to claim 5, wherein said ball-release piece has a flange portion arranged to fit snugly over one end of said ball holder.

7. A test apparatus according to claim 5 wherein said nibs of said ball-release piece are arranged to release one of said coated balls when said ball-release piece is pressed on its extended exterior surface at said opening.

8. A test apparatus according to claim 1 wherein said wells are hemispherical in shape.

9. A test apparatus according to claim 1 wherein said balls are polystyrene balls.

10. A test apparatus according to claim 1 wherein said wells are contoured to provide coverage of one of said coated balls with a minimum of a blood sample and to prevent the entrapment of air between said ball and the well.

* * * * *